United States Patent

Hirota et al.

[11] Patent Number: 5,922,946
[45] Date of Patent: Jul. 13, 1999

[54] PARTICLE SENSOR

[75] Inventors: Toshikazu Hirota, Kuwana; Kazuyoshi Shibata, Nagoya, both of Japan

[73] Assignee: NGK Insulators, Ltd., Japan

[21] Appl. No.: 08/879,020

[22] Filed: Jun. 19, 1997

[30] Foreign Application Priority Data

Jun. 25, 1996 [JP] Japan .................................. 8-164759

[51] Int. Cl.⁶ ................................................ G01N 15/06
[52] U.S. Cl. ......................................... 73/61.75; 73/61.71
[58] Field of Search ............................. 73/61.71, 61.75, 73/865.5; 310/324, 338; 348/627, 631

[56] References Cited

U.S. PATENT DOCUMENTS

| 3,656,253 | 4/1972 | Oliin ....................................... 73/61.75 |
| 4,432,228 | 2/1984 | Kuschmierz et al. ................... 310/338 |
| 5,698,931 | 12/1997 | Shibata et al. ........................... 310/338 |

FOREIGN PATENT DOCUMENTS

| 39 31 497 A1 | 4/1991 | European Pat. Off. . |
| 0 675 355 | 10/1995 | European Pat. Off. . |
| 0 753 348 A1 | 1/1997 | European Pat. Off. . |
| 0 766 086 A2 | 4/1997 | European Pat. Off. . |
| 0 769 695 A2 | 4/1997 | European Pat. Off. . |

*Primary Examiner*—Harshad Patel
*Assistant Examiner*—Robin Clark
*Attorney, Agent, or Firm*—Parkhurst & Wendel

[57] ABSTRACT

A particle sensor includes a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet. The particle sensor has a characteristic structure of having a net at the upstream side of the sensor element in order to allow the fluid entering the particle sensor from the fluid inlet to pass through said net and then contact with the sensor element. With this particle sensor, the detection of the solid particles contained in a fluid also containing bubbles can be made at a higher accuracy because the vibration caused by the bubbles, containing the primary resonance vibration of the sensor element is decreased.

8 Claims, 6 Drawing Sheets

PARTICLE SENSOR

BACKGROUND OF THE INVENTION

1. Field of the Invention

The present invention relates to a particle sensor for detecting the solid particles contained in a fluid.

2. Description of Related Art

When solid particles are present in a fluid (a liquid or a gas), it is necessary in some cases to detect the presence of the solid particles. Detection of such solid particles is particularly important when the solid particles present in the fluid badly affect the intended action of the fluid.

Lubricating oils (e.g. engine oils) are used in internal combustion engines of automobiles or heavy machinery in order to reduce the frictional resistance and abrasion of the rotating surfaces and sliding surfaces of the engines. Operation of such internal combustion engines generates solid particles (e.g. metal fine particles) caused by abrasion, and the solid particles are taken into the lubricating oils and accelerate, in some cases, the abrasion of the rotating surfaces and sliding surfaces. The solid particles, etc. present in the lubricating oils are ordinarily removed by the use of a filter such as oil filter or the like. The condition of the lubricating oils can be monitored in detail by detecting the solid particles present in the lubricating oils.

Hydraulic oils and flushing oils are used in power transmission mechanisms (e.g. transmission), oil hydraulic pipe systems (e.g. oil hydraulic servo valve), rolling, pressing, etc. It is important to control the condition of these oils by detecting the solid particles present in the oils and/or examining the viscosities of the oils.

It is also important to detect the particles suspended in the air or examine their concentration in the air in order to monitor the level of air pollution. Such detection includes detection of the particles suspended in the exhaust gas discharged from a plant, a factory or the like.

The applicant proposed, as a sensor for detecting solid particles contained in a fluid, an axial flow particle sensor comprising:

a sensor element comprising (a) a vibrating section having such a mass that is sensitive to the collision of solid particles contained in a fluid, with the vibrating section and (b) a detecting and converting section for detecting the vibration of the vibrating section caused by said collision and converting the vibration to electric signals, a housing for fixing said sensor element, a fluid inlet, and a fluid outlet, in which axial flow particle sensor said fluid outlet is provided so that the sensor element is between the fluid inlet and the fluid outlet, throughholes are formed in the sensor element in at least part of the vicinity of the vibrating section, and the vibrating section of the sensor element is provided in the stream of the fluid formed by the fluid inlet so that the fluid from the fluid inlet can pass through the throughholes and leave the particle sensor from the fluid outlet (European Patent Publication 0769695-A2).

Figure 5:
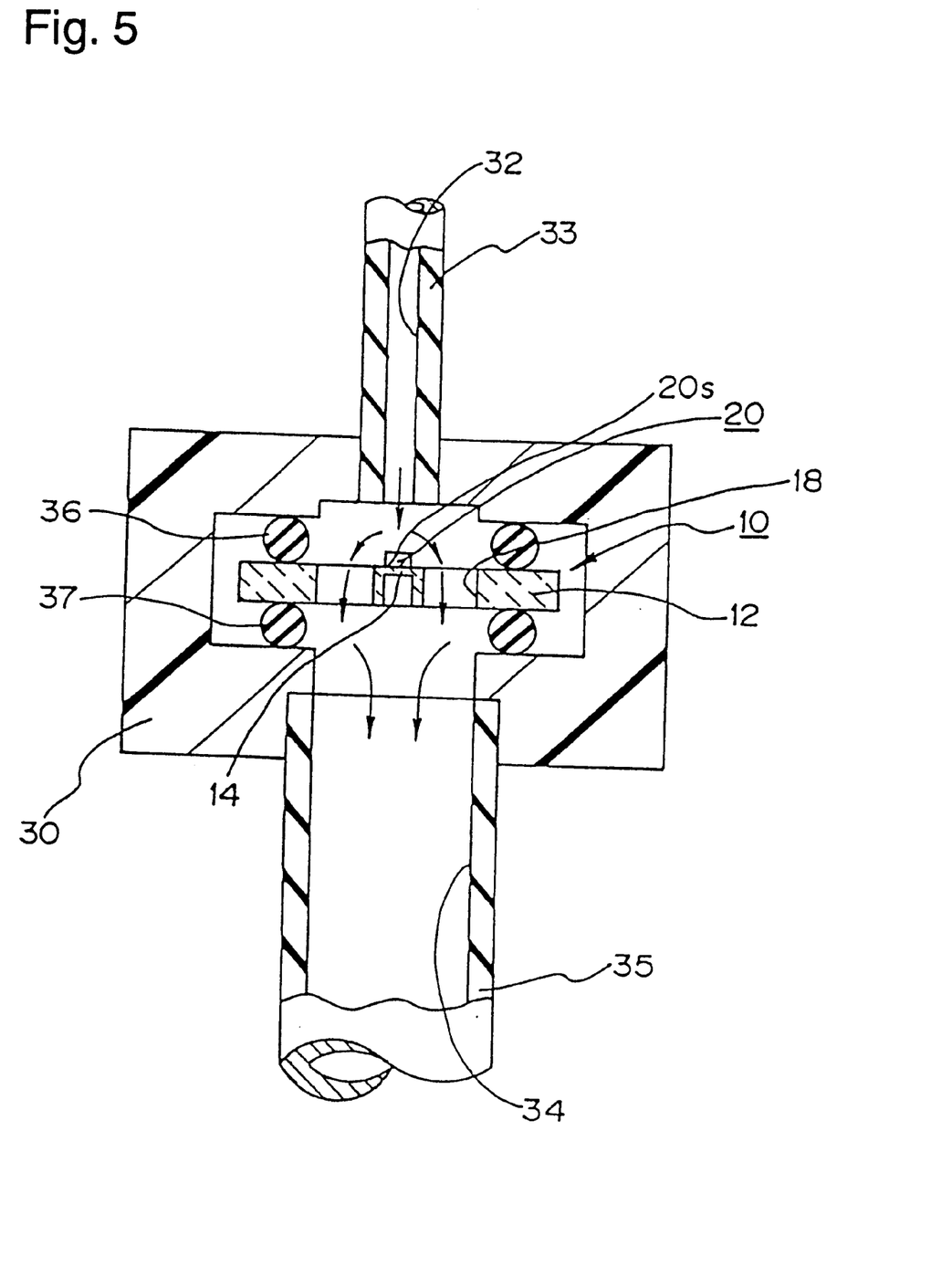
FIG. 5 shows an example of the basic structure of the particle sensor.

FIG. 5 shows an example of the structure of the above axial flow particle sensor. In this structure, the flow path of a fluid is constituted by a nozzle 33 forming the inlet 32 of the fluid, a nozzle 35 forming the outlet of the fluid, and a housing 30 to which the nozzles 33 and 35 are fixed and which accommodates a sensor element 10 between the nozzles 33 and the nozzle 35. The sensor element 10 is fixed to the inside of the housing 30 via elastic members 36 and 37 (e.g. o-rings).

Figure 6:
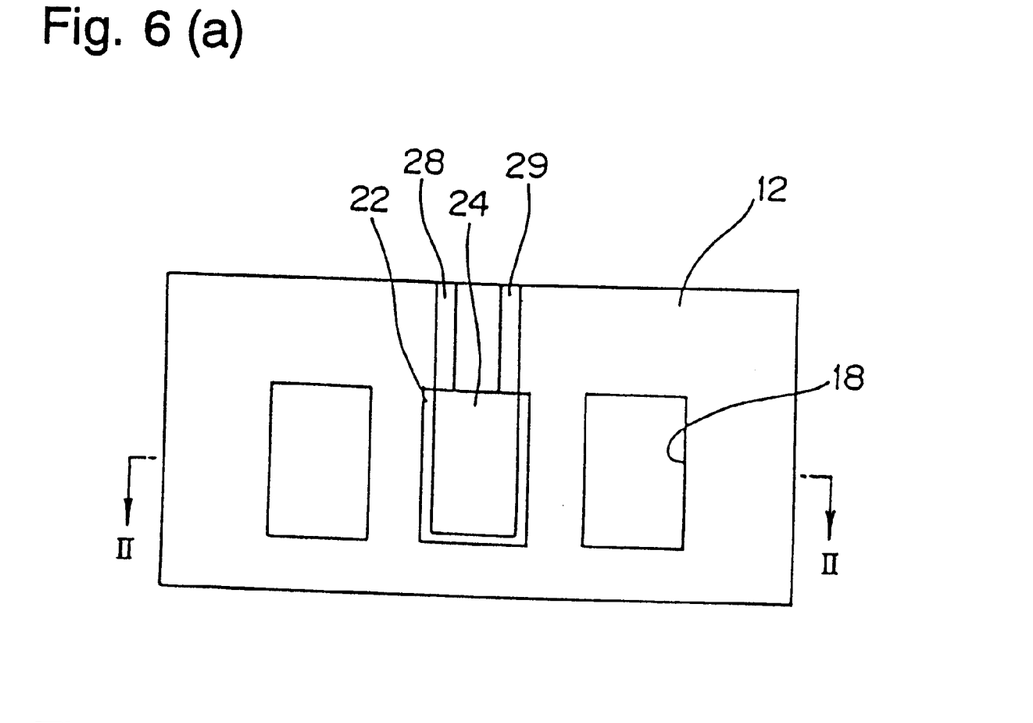
FIG. 6(a) is a plan view and FIG. 6(b) is a sectional view taken at the II—II line of FIG. 6(a).

FIGS. 6(a) and 6(b) show an example of the sensor element used in the above axial flow particle sensor. FIG. 6(a) is a plan view of the sensor element and FIG. 6(b) is a sectional view of the sensor element taken at the II—II line of FIG. 6(a). The vibrating section 14 is a thin plate and is fixed to a fixing section 16 so that the vibrating section 14 can vibrate, whereby the vibrating section 14 and the fixing section 16 forms a one-piece body 12. A hollow 17 is formed in the body 12 so that the vibrating section 14 can become a thin plate. On one surface 14s of the vibrating section 14 opposite to its surface facing the hollow 17 is provided a detecting section 20. In the portion of the body in the vicinity of the vibrating section 14 are formed a pair of throughholes 18 penetrating the body 12 in the thickness direction.

In FIG. 5, a fluid enters the housing 30 through the nozzle 33 and contacts with the vibrating section 14 and the detecting section 20 mounted on the vibrating section 14, in such a way that the fluid flow is interrupted by the contact as shown by the arrows. At this time, the solid particles present in the fluid collide with the vibrating section 14 and the detecting section 20, whereby the vibrating section 14 and the detecting section 20 vibrate. After contact with the vibrating section 14 and the detecting section 20, the fluid passes through the throughholes 18, passes through the nozzle 35, and leaves the sensor. With this particle sensor, solid particles present in a fluid collide with the detecting section 20 (having a piezoelectric film) of the sensor element or with the vibrating section 14 (mounting the detecting section 20 thereon) of the sensor element; thereby, the vibrating section 14 and the detecting section 20 are vibrated; the piezoelectric film 22 converts the vibration into electric signals; the electric signals are outputted by electrodes 24, 26 holding the piezoelectric film between them.

In detecting solid particles present in a fluid by the use of a particle sensor such as mentioned above, the fluid often contains bubbles besides the solid particles when the fluid is a liquid such as oil or the like. The vibrating section of the particle sensor is vibrated as well by the collision of the bubbles and the signals of this vibration are outputted as well from the detecting section. To accurately know the concentration of solid particles in fluid, it is necessary to distinguish the signals given by the vibration caused by bubbles from the signals given by the vibration caused by solid particles.

Figure 7:
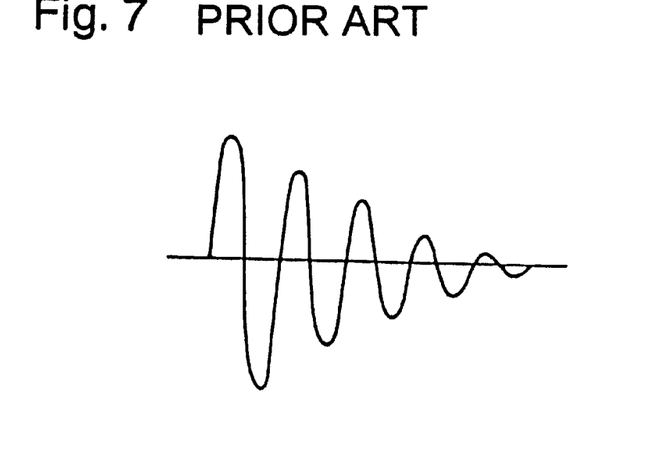
FIG. 7 is a waveform of the signals given by the vibration caused by collision of solid particles (the vibration is the primary resonance vibration of sensor element), obtained with a conventional particle sensor.
Figure 8:
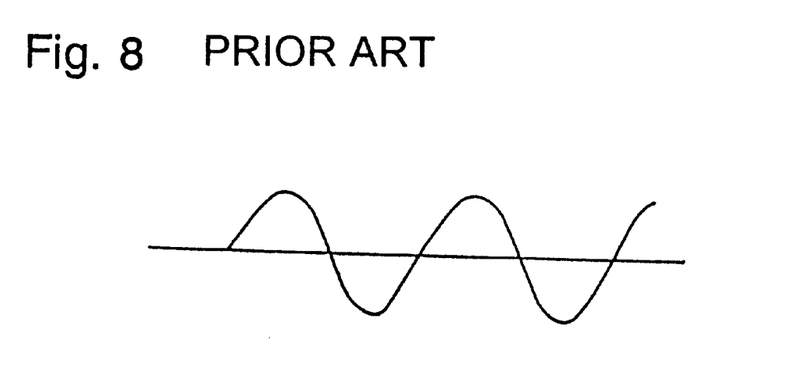
FIG. 8 is a waveform of the signals given by the vibration caused by collision of bubbles (the vibration is a long-period vibration of lower frequency than the primary resonance frequency of sensor element), obtained with a conventional particle sensor.

The vibration of the particle sensor caused by the collision of solid particles generally appears as the primary resonance vibration of the sensor element, such as shown by the signal waveform of FIG. 7. Meanwhile, the vibration of the particle sensor caused by collision of bubbles often appears as a long-period vibration having a frequency lower than the primary resonance frequency of the sensor element, such as shown by the signal waveform of FIG. 8.

Figure 9:
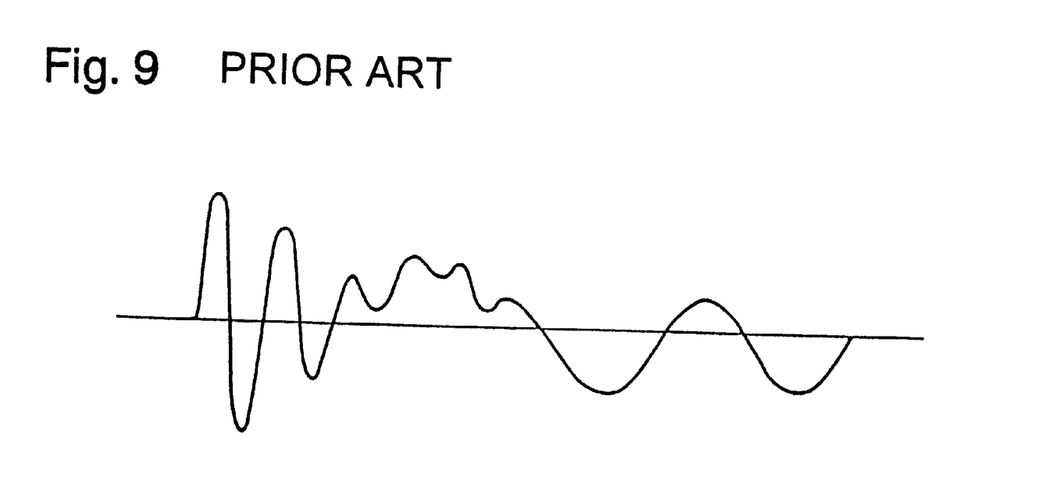
FIG. 9 is a waveform of the signals given by the vibration caused by collision of bubbles (the vibration contains the primary resonance vibration of sensor element), obtained with a conventional particle sensor.

However, collision of bubbles sometimes allows the vibrating section to cause vibrations containing the primary resonance vibration of the sensor element, such as shown by the signal waveform of FIG. 9. Such a vibration containing the primary resonance vibration of the sensor element, caused by bubbles is difficult to distinguish from a vibration caused by solid particles; this may result in taking of bubble-caused signals for particle-caused signals when a conventional sensor is used, and has been one reason for the lower accuracy of conventional sensors.

SUMMARY OF THE INVENTION

In view of the above situation, the present invention is intended to provide a particle sensor with which the detection of the solid particles contained in a fluid also containing bubbles can be made at a higher accuracy by decreasing the vibration caused by the bubbles, containing the primary resonance vibration of the sensor element.

According to the present invention, there is provided, as a first aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, which particle sensor has a characteristic structure of having a net at the upstream side of the sensor element in order to allow the fluid entering the particle sensor from the fluid inlet to pass through said net and then contact with the sensor element.

According to the present invention, there is provided, as a second aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, which particle sensor has a characteristic structure of having a means capable of increasing the inside-housing pressure.

According to the present invention, there is provided, as a third aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure of having a relation of $D/d \geq 1.5$ wherein d is the width of the detecting section and D is the distance from the center line of the detecting section to the throughhole closest to the detecting section.

According to the present invention, there is provided, as a fourth aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure of being chamfered at the periphery of the inlet of each throughhole of the sensor element.

According to the present invention, there is provided, as a fifth aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure that (1) the sensor element portion which contacts with the fluid from the fluid inlet and (2) the inner wall of each throughhole of the sensor element have a surface roughness of 0.40 $\mu$m or less in terms of Center-line Mean Roughness where high band cut-off value is 0.8 mm and a reference length is 2.5 mm.

According to the present invention, there is provided, as a sixth aspect of the invention, a particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure that the fluid from the fluid inlet contacts with the sensor element at an angle of less than 90° as measured relative to the sensor element surface.

BRIEF DESCRIPTION OF THE DRAWINGS

FIGS. 1(a) and 1(b) show an example of the sensor element of the particle sensor according to the third aspect of the invention.

FIGS. 6(a) and 6(b) show an example of the sensor element.

DETAILED DESCRIPTION OF THE PREFERRED EMBODIMENT

Regarding the vibration caused by bubbles present in a fluid, containing the primary resonance vibration of sensor element, which appears in the sensor element of particle sensor and is difficult to distinguish from the vibration caused by solid particles also present in the fluid, the present inventor made a study on the mechanism of generation of said bubbles-caused vibration. As a result, it was found out that the bubbles-caused vibration containing the primary resonance vibration of sensor element is generated not by the impact of direct collision of bubbles with the vibrating section or detecting section of sensor element, but by the bursting of bubbles on the sensor element or in its vicinity and subsequent propagation of the bursting impact to the vibrating section or detecting section.

The present invention has been completed based on the above finding. In the particle sensor of the present invention, the bursting of bubbles on the sensor element or in its vicinity is suppressed and thereby the propagation of the bursting impact to the vibrating section or detecting section of the sensor element is reduced; as a result, the vibration caused by bubbles, containing the primary resonance vibration of the sensor element (this bubbles-caused vibration is difficult to distinguish from the vibration caused by solid particles) is decreased and the detection of solid particles can be made at a higher accuracy. The present invention is described in detail below.

Description is made first on the particle sensor of the first aspect of the invention. The particle sensor of the first aspect of the invention can have a basic structure shown in FIG. 5. Besides, it has a characteristic structure of having a net at the upstream side of the sensor element 10 so that the fluid from the fluid inlet 32 can pass through the net and then contact with the sensor element 10.

By thus allowing the fluid to pass through the net before its contact with the sensor element, the relatively large bubbles in the fluid (which are easily bursted upon contact with the sensor element, etc.) are split by the meshes of the net into smaller bubbles (which are less likely to be bursted). As a result, the vibration caused by the bursting of bubbles, which is difficult to distinguish from the vibration caused by solid particles, decreases and resultantly the detection of solid particles can be made at a higher accuracy.

The lower limit of the meshes of the net is the diameter of solid particles to be detected, and the upper limit is preferably 1,000 μm or less, more preferably 100 μm or less, further preferably 50 μm or less. When the meshes of the net are smaller than the diameter of solid particles to be detected, the solid particles are unable to reach the sensor element; when the meshes of the net are too large, it is impossible to split the bubbles into a size which is less likely to be bursted.

A particle sensor having a basic structure shown in FIG. 5 is called an axial flow particle sensor. In this particle sensor, the sensor element 10 is provided between the fluid inlet 32 and the fluid outlet 34; throughholes 18 are formed in at least part of the vicinity of the vibrating section 14 of the sensor element 10; and the vibrating section 14 of the sensor element 10 is provided in the flow direction of the fluid determined by the fluid inlet 32 so that the fluid entering the particle sensor from the fluid inlet 32 can pass through the throughholes 18 and leave the particle sensor from the fluid outlet 34. Such a basic structure is preferably used in the particle sensor of the first invention; however, any other basic structure can be used as long as the fluid from the fluid inlet contacts with the sensor element and then leaves from the fluid outlet.

Next, description is made on the particle sensor of the second aspect of the invention. The particle sensor of the second aspect of the invention as well can have a basic structure shown in FIG. 5. Besides, it has a characteristic structure of having a means capable of increasing the pressure inside the housing 30. When the pressure inside the housing 30 wherein the sensor element 10 is accommodated and fixed, is increased by the action of said means, the bubbles contained in a fluid is destroyed or made into a smaller size which is not easily bursted by the pressure increase, in the vicinity of the sensor element 10. As a result, the vibration caused by the bursting of bubbles, which is difficult to distinguish from the vibration caused by solid particles, decreases and the detection of solid particles can be made at a higher accuracy.

The means capable of increasing the pressure inside the housing 30 can include a valve provided at the downstream side of the sensor element 10. By using this valve to decrease the flow amount of fluid at the fluid outlet (the minimum flow amount required must be secured), the pressure inside the housing in the upstream of the valve can be increased. Preferably, the valve is provided not near the sensor element 10 but at a place at least 10 cm apart from the sensor element 10. When the valve is provided apart from the sensor element 10, the vibration of fluid per se occurring in the flow amount-decreased fluid portion is unlikely to propagate to the sensor element 10, whereby the vibration of fluid per se is not detected substantially. The means capable of increasing the pressure inside the housing is not restricted to the valve.

The inside-housing pressure increased by the above means is preferably higher than 1.0 kg/cm$^2$, more preferably 1.5 kg/cm$^2$ or more, further preferably 3.0 kg/cm$^2$ or more.

Similarly to the basic structure of the particle sensor of the first aspect of the invention, the basic structure of the particle sensor of the second aspect of the invention is not restricted to that of axial flow particle sensor and can be any other structure as long as it can allow the fluid from the fluid inlet to contact with the sensor element and then leave from the fluid outlet.

Figure 1:
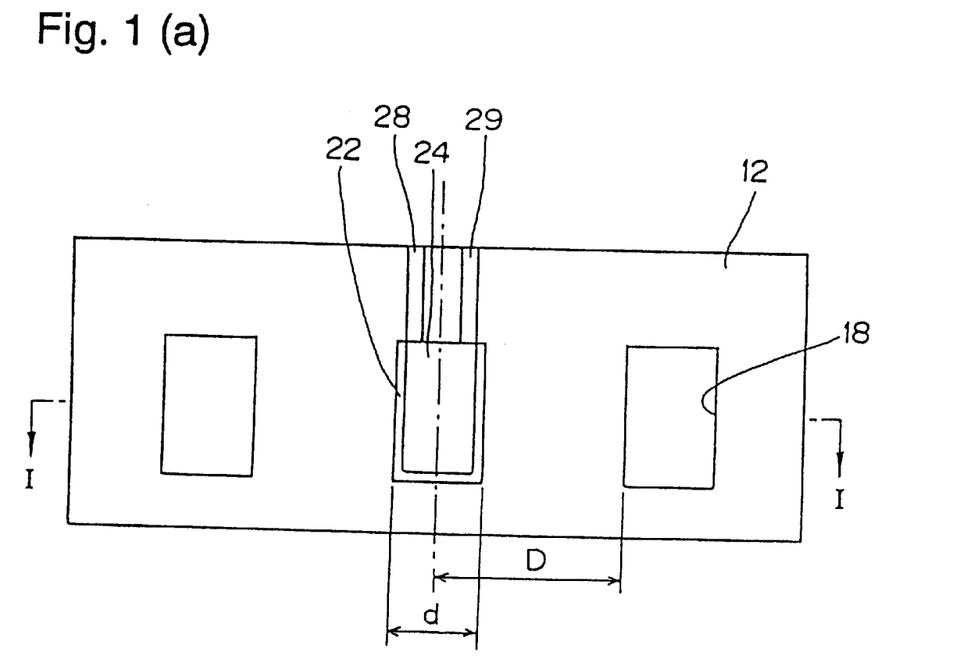
FIG. 1(a) is a plan view and FIG. 1(b) is a sectional view taken at the I—I line of FIG. 1(a).

The particle sensor of the third aspect of the invention as well has a basic structure shown in FIG. 5. Besides, it has a characteristic structure of having a relation of D/d≧1.5, preferably D/d≧2.0 wherein d is the width of the detecting section 20 of the sensor element 10 and D is the distance from the center line of the detecting section 20 to the throughhole 18 closest to the detecting section, as shown in FIG. 1(*a*) (a plan view) and FIG. 1(*b*) [a sectional view taken at the I—I line of FIG. 1(*a*)].

A study was made by the present inventor in order to know in what part of a conventional axial flow particle sensor the bubbles contained in a fluid are easily bursted. As a result, it was found out that the bubbles are bursted most easily in the vicinity of the throughholes 18 formed near the vibrating section 14. The third aspect of the invention was completed based on this finding. That is, in the third aspect of the invention, the throughholes 18 are provided apart from the detecting section 20 so that even when the bursting of bubbles occurs in the vicinity of the throughholes 18, the impact of bubble bursting does not easily propagate to the detecting section.

The investigation made on the width of the detecting section 20 as well as on the distance from the detecting section 20 to the throughholes 18 revealed that when a relation of D/d≧1.5 is satisfied, the impact of bubbles bursted in the vicinity of the throughholes 18 does not easily propagate to the detecting section 20. When the above relation is satisfied, even when the bursting of bubbles occurs in the vicinity of the throughholes 18, the impact of the bursting hardly vibrates the vibrating section 14 or the detecting section 20 and, resultantly, the detection of solid particles can be made at a higher accuracy.

Figure 2:
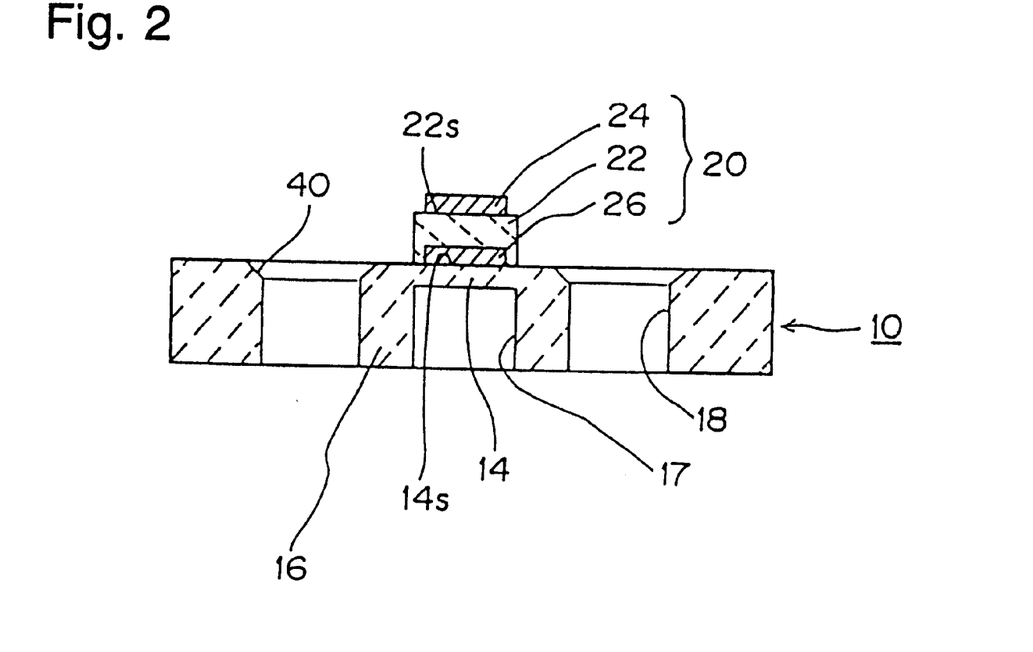
FIG. 2 is a sectional view showing an example of the sensor element of the particle sensor according to the fourth aspect of the invention.

The particle sensor of the fourth aspect of the invention as well has a basic structure shown in FIG. 5. Besides, it has a characteristic structure of being chamfered at the periphery of the inlet of each throughhole of the sensor element and having a chamfered portion 40, as shown in FIG. 2.

As mentioned previously, the bursting of bubbles appears at the highest probability in the vicinity of each throughhole 18 formed around the vibrating section 14. These throughholes 18 are provided so that the fluid from the fluid inlet, after being contacted with the sensor element, can move toward the fluid outlet. By chamfering the inlet of each throughhole 18, the flow of fluid into throughhole 18 becomes smooth and the bubbles contained in the fluid are bursted at a lower probability. As a result, the vibration caused by the bursting of bubbles, which is difficult to distinguish from the vibration caused by solid particles, decreases and the detection of solid particles can be made at a higher accuracy. Chamfering is preferably made at the whole periphery of the inlet of each throughhole 18, but the chamfering effect is obtained to some extent even when the periphery of the inlet is chamfered partially.

The particle sensor of the fifth aspect of the invention as well has a basic structure shown in FIG. 5. Besides, it has a characteristic structure that (1) the sensor element portion which contacts with the fluid from the fluid inlet and (2) the inner wall of each throughhole 18 of the sensor element have a surface roughness of 0.40 $\mu$m or less, preferably 0.20 $\mu$m or less in terms of Center-line Mean Roughness where high band cut-off value is 0.8 mm and a reference length is 2.5 mm.

In this particle sensor, since (1) the sensor element portion which contacts with the fluid from the fluid inlet and (2) the inner wall of each throughhole of the sensor element have a surface roughness mentioned above, the frictional resistance appearing when the fluid contacts with the portion (1) and the inner wall (2) is small and, as a result, the flow of the fluid is smooth and the bursting of bubbles contained in the fluid appears at a lower probability. As a result, the vibration caused by the bursting of bubbles, which is difficult to distinguish from the vibration caused by solid particles, descreases and the detection of solid particles can be made at a higher accuracy.

The above-mentioned surface roughness can be obtained in the process (to be described later) for making the present sensor element, as follows, for example. That is, a sensor element (a body and a detecting section) before sintering is subjected to a surface-smoothening treatment by controlling the conditions for molding a green sheet for body or the conditions for forming a piezoelectric film or an electrode film which are both to constitute the detecting section of sensor element; alternatively, a sensor element after sintering can be subjected to surface grinding or annealing.

Figure 3:
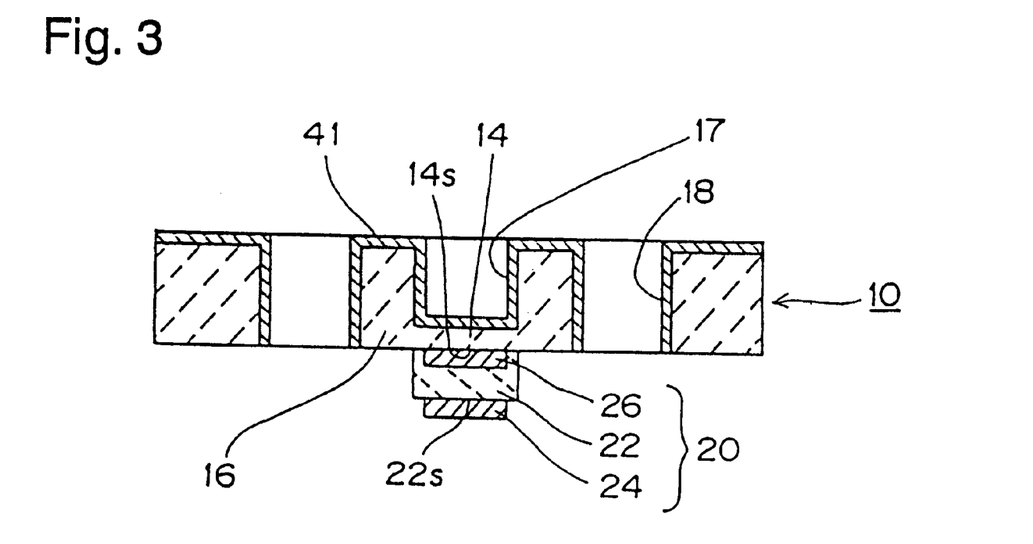
FIG. 3 is a sectional view showing an example of the sensor element of the particle sensor according to the fifth aspect of the invention.

The above-mentioned surface roughness can be obtained more easily by the following method. That is, the surface of the sensor element portion which contacts with the fluid from the fluid inlet and the surface of the inner wall of each throughhole 18 are coated with a resin (e.g. epoxy resin, polyimide resin, phenolic resin or silicone resin), water glass, a metal alkoxide or the like, whereby the roughness of said surfaces can be improved. FIG. 3 shows an example in which the surface of the sensor element portion which contacts with the fluid from the fluid inlet and the surface of the inner wall of each throughhole 18 are coated with a resin 41.

In coating said surfaces with a resin or the like, it is preferable to provide the detecting section 20 at the side of the sensor element facing the fluid outlet, as shown in FIG. 3 [in FIG. 3, the fluid outlet (not shown) is at the bottom side of FIG. 3]. When the detecting section 20 is provided at the side of the sensor element facing the fluid inlet, the surface of the detecting section 20 is coated with a resin or the like, reducing the sensitivity of the sensor element.

Figure 4:
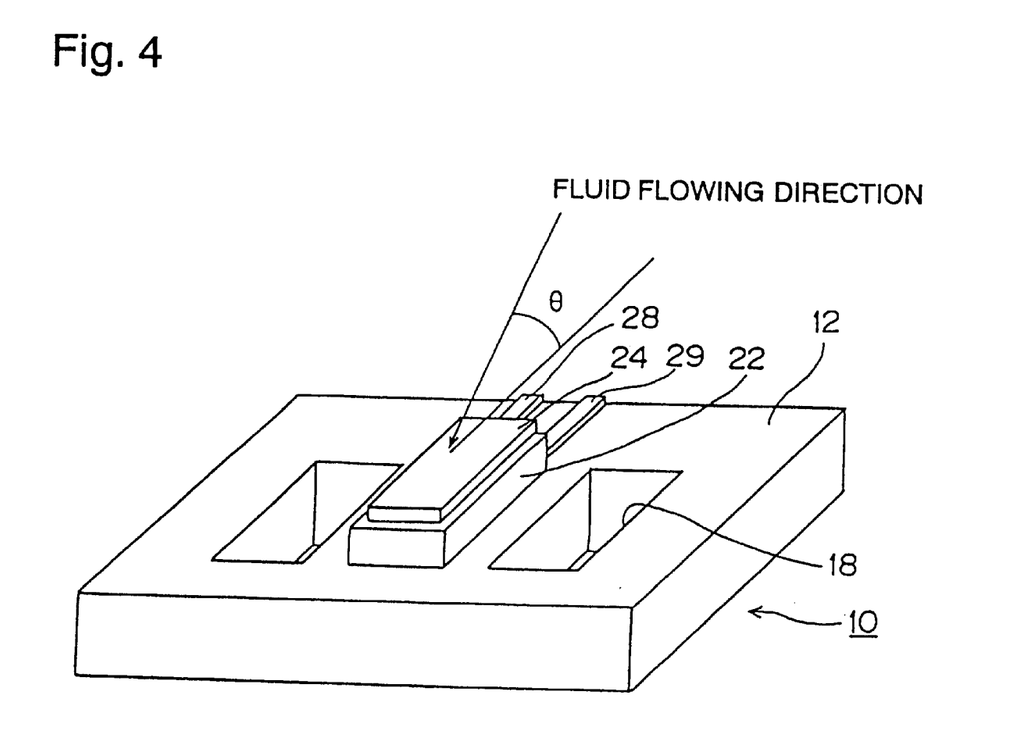
FIG. 4 is a perspective view showing an example of the sensor element of the particle sensor according to the sixth aspect of the invention.

The particle sensor of the sixth aspect of the invention as well has a basic structure shown in FIG. 5. Besides, it has a characteristic structure that the fluid from the fluid inlet contacts with the sensor element at an angle θ of less than 90°, preferably less than 60° as measured relative to the sensor element surface, as shown in FIG. 4.

By thus setting the contact angle of the fluid to the sensor element, the impact generating when the bubbles contained in the fluid collide with the sensor element, is made smaller and the bursting of bubbles on sensor element is suppressed. As a result, the vibration caused by the bursting of bubbles, which is difficult to distinguish from the vibration caused by solid particles, decreases and the detection of solid particles can be made at a higher accuracy.

The above setting of the contact angle of the fluid to the sensor element can be made by controlling, for example, the fixing angle of sensor element to housing inside or the fixing angle of nozzle (for inlet formation) to housing.

The first to sixth aspects of the invention explained above can be used in any desired combination. For example, the first and second aspects of the invention can be combined to obtain a particle sensor having a net provided at the upsteam side of the sensor element and further a means for increasing the pressure inside the housing. Or, the third and fourth aspects of the invention can be combined to obtain a particle sensor wherein the width d of the detecting section of the sensor element and the distance D from the center line of the detecting section to the throughhole closest to the detecting section have a relation of $D/d \geq 1.5$ and wherein chamfering is made at the periphery of the inlet of each throughhole.

Next, description is made in detail on the constitution of each section of the sensor element used in the particle sensor of the present invention. The sensor element used in each of the present particle sensors has the same basic structure as used conventionally, except for the characteristic structures mentioned above for each of the first to sixth particle sensors. That is, as shown in FIGS. 6(a) and 6(b), the body 12 of the sensor element 10 has a hollow 17 in order to make thin the vibrating section 14, and throughholes 18 are formed around the vibrating section 14.

The vibrating section 14 need not be fixed to the fixing section 16 at the whole periphery as shown in FIG. 6(b), and may be fixed partially. For example, only one end of the whole periphery of the vibrating section 14 may be fixed to the fixing section 16. The hollow 17 is not restricted to such a hollow as shown in FIG. 6(b) and may be a closed space. The hollow may be formed at the outlet 34 side, or may be formed at the inlet 32 side. The detecting section 20 may be provided at the inlet 32 side relative to the vibrating section 14, or may be provided at the outlet 34 side relative to the vibrating section 14.

There is no particular restriction as to the number, shape, etc. of the throughholes 18. However, it is preferable that one pair of the throughholes 18 have the same shape and are provided symmetrically with respect to a virtual plane penetrating the vibrating section 14 in the axial direction. The shape of the body 12 is preferably a plate, but has no particular restriction and can be appropriately determined depending upon the intended application of particles sensor.

The vibrating section 14, when collided by solid particles or bubbles, vibrates, together with the detecting section 20, in a vertical direction, i.e. a direction extending to the detecting section 20 and the hollow 17. In order to detect this vibration advantageously, the vibrating section 14 is preferably a plate. The thickness of the vibrating section 14 is preferably 1–100 $\mu$m. When the thickness is more than 100 $\mu$m, the vibrating section has a low sensitivity to collision; when the thickness is less than 1 $\mu$m, the vibrating section has low mechanical strengths.

The vibrating section 14 is preferably composed of materials which are chemically stable and which undergo no chemical change in contact with various fluids containing solid particles to be detected. The vibrating section 14 is preferably made of a ceramic such as stabilized zirconia, partially stabilized zirconia, magnesia, mullite, aluminum nitride, silicon nitride, glass or the like. The fixing section 16 may be made of the same materials as used in the vibrating section 14, or of different materials.

The detecting section 20 has a piezoelectric film 22, a first electrode 24 and a second electrode 26 with the piezoelectric film being sandwiched between the two electrodes. The first electrode 24 covers at least part of the surface 22s of the piezoelectric film 22, and the second electrode 26 covers at least part of the surface 14s of the vibrating section 14. The piezoelectric film 22 causes, microscopically, dielectric polarization when a stress is applied thereto, and generates, macroscopically, an electric signal (e.g. electric charge or voltage) depending upon the level of the stress. At this time, it is preferable that the piezoelectric film undergoes bending displacement in the thickness direction.

The piezoelectric film 22, when the solid particles and bubbles present in a fluid contact with the first electrode 24 and/or the vibrating section 14, vibrates in its thickness direction together with the vibrating section 14. This vibration applies stress to the piezoelectric film 22, whereby the piezoelectric film 22 generates electric signals. The electric signals are outputted to terminal pads by the first electrode 24 and the second electrode 26 via leads 28 and 29.

The piezoelectric film 22 has a thickness of preferably 1–100 $\mu$m. When the thickness is more than 100 $\mu$m, the film has a low sensitivity; when the thickness is less than 1 $\mu$m, the film has no sufficient reliability.

Preferably, the piezoelectric film is made of a piezoelectric ceramic. It may also be made of an electrostrictive ceramic or a ferroelectric ceramic. Or, it may be made of a material which needs a polarization treatment or no polarization treatment.

The ceramic used in the piezoelectric film includes, for example, a ceramic containing lead zirconate, magnesium lead niobate, nickel lead niobate, zinc lead niobate, manganese lead niobate, antimony lead stannate, lead titanate, manganese lead tungstate, cobalt lead niobate, barium titanate, or any combination thereof.

The above ceramic may further contain an appropriate amount of an oxide of lanthanum, calcium, strontium, molybdenum, tungsten, barium, niobium, zinc, nickel, manganese or the like; any combination of said oxides; or other compound. For example, a ceramic composed mainly of magnesium lead niobate, lead zirconate and lead titanate and further containing lanthanum or strontium is preferred.

The first electrode and the second electrode can have appropriate thicknesses depending upon the application of the present particle sensor, but each thicknesses is preferably 0.1–50$\mu$.

The first electrode is preferably composed of an electroconductive metal which is a solid at room temperature. The metal includes, for example, single metals such as aluminum, titanium, chromium, iron, cobalt, nickel, copper, zinc, niobium, molybdenum, ruthenium, rhodium, silver, tin, tantalum, tungsten, iridium, platinum, gold, lead and the like; and their alloys.

The second electrode is preferably composed of a high-melting metal such as platinum, ruthenium, rhodium, palladium, iridium, titanium, chromium, molybdenum, tantalum, tungsten, nickel, cobalt or the like; or any alloy thereof. It is because the second electrode may be exposed to high temperatures when the piezoelectric film is subjected to a heat treatment and therefore the second electrode is preferably made of a metal resistive to a high-temperature oxidizing atmosphere. The second electrode may be made of a cermet composed of the above-mentioned high-melting metal and a ceramic such as alumina, zirconium oxide, silicon oxide, glass or the like.

Next, description is made on the process for producing the sensor element of the present particle sensor.

The body of the sensor element is made in one piece by laminating a plurality of laminating layers (which are green sheets or green tapes) by hot pressing or the like and then sintering the laminate. For example, in the body 12 of FIG. 6(b) having a hollow 17, two laminating layers of green sheets or green tapes are laminated; before the lamination, a throughhole of desired shape to become the hollow 17 is formed in the second layer. Alternatively, the layers may be formed by pressure molding, casting, injection molding or the like and the hollow may be formed by cutting, machining, laser processing, punching by pressing or the like. Although the laminating layers need not have the same thickness, it is preferred that the layers undergo similar shrinkages in sintering.

Formation of a detecting section 20 on the ceramic vibrating section 14 can be conducted as follows. A piezoelectric is formed by pressing using a mold or by tape forming using a material slurry; this piezoelectric before sintering is laminated on the vibrating section of the body before sintering by hot pressing; and sintering is conducted to form a body and a piezoelectric. In this case, electrodes must be formed on the body or the piezoelectric beforehand by a film forming method described later.

Although the sintering temperature for the piezoelectric film is determined appropriately depending upon the materials of the film, the sintering temperature is generally 800–1,400° C., preferably 1,000–1,400° C. In this case, it is preferred for controlling the composition of the piezoeletric film to conduct sintering in the presence of the evaporation source of the components of the piezoeletric film.

In the film forming method, a second electrode 26, a piezoelectric film 22 and a first electrode 24 are laminated in this order on the vibrating section 14 to form a detecting section 20. As the film forming method, there can be appropriately used a known forming method, for example, a thick film method (e.g. screen printing), a coating method (e.g. dipping) or a thin film method [e.g. ion beam, sputtering, vacuum deposition, ion plating, chemical vapor deposition (CVD) or plating]. However, the film forming method is not restricted to these methods. Among these methods, screen printing is preferred because of stable production.

A second electrode 26, leads 28 and 29 and terminal pads can be simultaneously formed by screen printing. A piezoelectric film 22 is preferably formed by screen printing, dipping or the like. In these methods, a piezoelectric film can be formed on the body using a paste or a slurry each containing materials for piezoelectric film and composed mainly of ceramic particles, whereby the piezoelectric film can have good properties.

When a piezoelectric film is formed by a film forming method, since the detecting section and the vibrating section can be bonded integrally without using any adhesive, this method is especially preferred because of the high reliability, reproducibility and integratability. A piezoelectric film may be formed in an appropriate pattern. The pattern may be formed by screen printing, photolithography or the like, or may be formed by removing unnecessary portions using mechanical processing such as laser processing, slicing, ultrasonic processing or the like.

Each film (22, 24 and 26) thus formed on the body may be made integral with the body by heat treatment each time one film is formed, or by heat-treating these films simultaneously after formation of all films. When the first and second electrodes are formed by a thin film method, heat treatment is not always necessary for their integration.

Throughholes 18 may be formed in the green sheets or green tapes or in the laminating layers.. obtained using a mold, at the time of body formation, by mechanical processing such as cutting, grinding, punching by pressing, or the like. That is, green sheets or the like may be machined so as to form throughholes of desired shape. Throughholes may also be formed by mechanical processing such as laser processing, cutting, ultrasonic processing or the like, after sintering of the body. Throughholes may also be formed after forming a detecting section, using the same processing method.

The detecting section of the present particle sensor was explained in the above, focussing on a device utilizing the piezoelectricity of a piezoelectric film, which device detects the vibration of the vibrating section and converts the vibration into electric signals by piezoelectricity of the film. However, the detecting section is not restricted to the above device utilizing piezoelectricity.

For example, the detecting section may be a device utilizing electromagnetic induction. This device comprises a coil provided on the vibrating section, an electric circuit for detecting electric signals flowing through this coil, and a magnet (which may be an electromagnet) forming a magnetic field in the coil. When the coil vibrates together with the vibrating section, a current flows through the coil owing to electromagnetic induction and is detected by the electric circuit.

The detecting section may be a device utilizing change in static capacity. This device comprises a pair of electrodes provided on the vibrating section, a dielectric held between the electrodes, and an electric circuit connected to the electrodes, and the static capacity stored in this specific space is detected by the electric circuit.

The detecting section may be a device utilizing change in reflected light amount. This device has a means (e.g. a photodiode) for applying a light to the vibrating section and a means for measuring the amount of light reflected by the vibrating section. The means for measuring the amount of light reflected by the vibrating section includes a photosensor. As the vibrating section vibrates, the amount of light reflected by the vibrating section changes, and this change in reflected light amount is measured.

The detecting section may be a device utilizing change in electric resistance caused by the strain of a conductor. This device has a conductor provided on the vibrating section and an electric circuit connected to this conductor. When the conductor vibrates together with the vibrating section, the conductor is strained by the vibration and its resistance changes, and this change in resistance is detected by the electric circuit.

The detecting section may be a device utilizing change in electric resistance caused by the strain of a semiconductor. This device has a semiconductor provided on the vibrating section, and an electric circuit connected to this semiconductor. When the semiconductor vibrates together with the vibrating section, the semiconductor is strained by the vibration and its resistance changes, and this change in resistance is detected by the electric circuit.

EXAMPLES

The present invention is described more specifically by way of Examples. However, the present invention is not restricted to these Examples.

There were produced particle sensors No. 1 to No. 10 having the basic structure shown in FIG. 5 and having a constitution shown in Table 1. Each of the particle sensors was placed in a line through which a test fluid flowed, and measured for ratio of resonance vibration and sensitivity to solid particles. The results are shown in Table 1. Each item of Table 1 is explained below in detail.

Use of Net

When a particle sensor had a net having a 44-$\mu$m mesh diameter at the upstream side of the sensor element so that the fluid from the fluid inlet could pass through the net and then contact with the sensor element, an expression of "Yes"

was given. When a particle sensor had no such net, an expression of "No" was given.

Internal Pressure

The particle sensors No. 3, No. 8 and No. 9 had a valve at the downstream side of the sensor element. With this valve, the amount of the fluid leaving the fluid outlet was decreased, whereby the pressure inside the housing accommodating the sensor element was increased to 3 kg/cm$^2$. Other particle sensors were provided with no such valve.

D/d

This is a ratio (D/d) of the distance (D) from the center line of the detecting section of the sensor element of a particle sensor to the throughhole closest to the detecting section, to the width (d) of the detecting section [see FIGS. 1(a) and 1(b)].

Chamfering

In some of the particle sensors, the inlet of each throughhole of the sensor element was chamfered at the whole periphery (see FIG. 2). For such particle sensors, an expression of "Yes" was given. For those particle sensors to which no chamfering was applied, an expression of "No" was given.

Surface Coating

In the particle sensor No. 6, (1) the surface area of the sensor element with which a fluid was to contact and (2) the inner wall surface of each throughhole of the sensor element were coated with an epoxy resin so as to give a Center-line Mean Roughness where high band cut-off value is 0.8 mm and a reference length is 2.5 mm of 0.15 μm (see FIG. 3). For this particle sensor, an expression of "Yes" was given. For other particle sensors to which no epoxy resin coating was applied and which had a Center-line Mean Roughness where high band cut-off value is 0.8 mm and a reference length is 2.5 mm of 0.5 μm at the sensor element surface and the inner wall surface of each throughhole of the sensor element, an expression of "No" was given.

Contact Angle of Fluid

By controlling the angle at which the sensor element of a particle sensor was fixed to the inside of the housing, a fluid from the fluid inlet was allowed to contact with the surface of the sensor element at a given angle (see FIG. 4).

Ratio of Resonance Vibration

A hydraulic oil containing no particle was used as a test fluid; the test fluid was passed through a particle sensor, and the electric signals given by bubbles contained in the test fluid was detected; and there was determined a ratio of (1) signals of vibrations containing the primary resonance vibration of sensor element to (2) total signals (signals of vibrations containing the primary resonance vibration of sensor element and signals of long-period vibrations of lower frequencies than that of the primary resonance vibration of sensor element). This ratio was converted to a relative value when the ratio given by the particle sensor No. 1 (a conventional particle sensor) was taken as 100. When the ratio is smaller, the primary resonance vibration caused by the bursting of bubbles takes place less frequently and the probability of taking the signals caused by bubbles for the signals caused by solid particles is smaller.

Sensitivity to Solid Particles

A hydraulic oil containing solid particles of given size (particle diameter: 40 μm) in a given concentration (10 particles/ml) was used as a test fluid; this test fluid was allowed to contact with the sensor element of a particle sensor at a given speed (5 m/s); the amplitude (voltage) of the signals detected by the sensor was examined. The amplitude was converted into a relative value when the amplitude obtained with the particle sensor No. 1 (a conventional particle sensor) was taken as 1.

TABLE 1

| No. of particle sensor produced | Use of net | Internal pressure (kg/cm$^2$) | D/d | Chamfering | Surface coating | Contact angle of fluid | Ratio of resonance vibration | Sensitivity to solid particles | Remarks |
|---|---|---|---|---|---|---|---|---|---|
| 1 | No | 1 | 1 | No | No | 90° | 100 | 1 | A conventional particle sensor |
| 2 | Yes | 1 | 1 | No | No | 90° | 20 | 1 | A particle sensor according to the first invention |
| 3 | No | 3 | 1 | No | No | 90° | 80 | 1 | A particle sensor according to the second invention |
| 4 | No | 1 | 2 | No | No | 90° | 60 | 1 | A particle sensor according to the third invention |
| 5 | No | 1 | 1 | Yes | No | 90° | 55 | 0.5 | A particle sensor according to the fourth invention |
| 6 | No | 1 | 1 | No | Yes | 90° | 30 | 0.2 | A particle sensor according to the fifth invention |
| 7 | No | 1 | 1 | No | No | 45° | 50 | 0.8 | A particle sensor according to the sixth invention |
| 8 | Yes | 3 | 1 | No | No | 90° | 5 | 1 | A particle sensor which is a combination of the first and second inventions |
| 9 | Yes | 3 | 2 | No | No | 90° | 1 | 1 | A particle sensor which is a combination of the first, second and third inventions |
| 10 | No | 1 | 2 | Yes | No | 90° | 30 | 0.5 | A particle sensor which is a combination of the third and fourth inventions |

As stated above, with the particle sensor of the present invention, the bursting of bubbles can be suppressed, or the impact generated by the bursting of bubbles is propagated to the detecting section of the sensor element less frequently. Therefore, the vibration caused by the bursting of bubbles, containing the primary resonance vibration of sensor element, which is difficult to distinguish from the vibration caused by the collision of solid particles, is decreased; as a result, the probability of taking the signals caused by bubbles, for the signals caused by solid particles is reduced and the detection of solid particles can be made at a higher accuracy.

What is claimed is:

1. A particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, which particle sensor has a characteristic structure of having a net at the upstream side of the sensor element in order to allow the fluid entering the particle sensor from the fluid inlet to pass through said net and then contact with the sensor element.

2. A particle sensor sensitive to collisions of solid particles contained in a fluid comprising:

a sensor element comprising (a) a vibrating section having such a mass that it is sensitive to collisions of solid particles contained in a fluid, with the vibrating sections and (b) a detecting section for detecting vibration of the vibrating section caused by said collisions and converting the vibration to electric signals, housing for said sensor element, fluid inlet, a fluid outlet, and means capable of increasing the inside-housing pressure which increases the fluid pressure to destroy or reduce the size of bubbles in the fluid so that they are not easily burst in the vicinity of the sensor element by the pressure increase, for increasing the amount of detection of solid particles in a fluid also containing bubbles.

3. A particle sensor according to claim 2, wherein the means capable of increasing the inside-housing pressure is a valve provided at the downstream side of the sensor element.

4. A particle sensor according to claim 2, wherein the means capable of increasing the inside-housing pressure can increase the inside-housing pressure to at least 1.5 kg/cm$^2$.

5. A particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure of having a relation of $D/d \geq 1.5$ wherein d is the width of the detecting section and D is the distance from the center line of the detecting section to the throughhole closest to the detecting section.

6. A particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure of being chamfered at the periphery of the inlet of each throughhole of the sensor element.

7. A particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure that (1) the sensor element portion which contacts with the fluid from the fluid inlet and (2) the inner wall of each throughhole of the sensor element have a surface roughness of 0.40 $\mu$m or less in terms of Center-line Mean Roughness where high band cut-off value is 0.8 mm and a reference length is 2.5 mm.

8. A particle sensor comprising:

a sensor element comprising (a) a vibrating section having such a mass that is sensitive to the collision of solid particles contained in a fluid, with the vibrating section and (b) a detecting section for detecting the vibration of the vibrating section caused by said collision and converting the vibration to electric signals, a housing for fixing said sensor element, a fluid inlet, and a fluid outlet, in which particle sensor said fluid outlet is provided so that the sensor element is between the fluid inlet and the fluid outlet, throughholes are formed in the sensor element in at least part of the vicinity of the vibrating section, and the fluid entering the particle sensor from the fluid inlet contacts with the sensor element, passes through the throughholes and leaves the particle sensor from the fluid outlet, and which particle sensor has a characteristic structure that the fluid from the fluid inlet contacts with the sensor element at an angle of less than 90° as measured relative to the sensor element surface.

* * * * *